United States Patent
Grable et al.

(10) Patent No.: US 6,693,287 B2
(45) Date of Patent: *Feb. 17, 2004

(54) LASER IMAGING APPARATUS USING BIOMEDICAL MARKERS THAT BIND TO CANCER CELLS

(75) Inventors: Richard J. Grable, deceased, late of Plantation, FL (US), by Linda B. Grable, executor; Robert H. Wake, Cooper City, FL (US)

(73) Assignee: Imaging Diagnostic Systems, Inc., Plantation, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/966,730

(22) Filed: Oct. 1, 2001

(65) Prior Publication Data

US 2002/0114765 A1 Aug. 22, 2002

Related U.S. Application Data

(63) Continuation of application No. PCT/US99/04287, filed on Apr. 1, 1999.
(60) Provisional application No. 60/063,590, filed on Oct. 30, 1997, and provisional application No. 60/036,088, filed on Jan. 17, 1997.

(51) Int. Cl.$^7$ .............................................. G01N 21/64
(52) U.S. Cl. ............................... 250/459.1; 250/461.2; 600/426; 600/317
(58) Field of Search ......................... 250/459.1, 458.1, 250/461.1, 461.2; 600/425, 426, 427, 317; 604/20; 356/317

(56) References Cited

U.S. PATENT DOCUMENTS

| 5,205,291 | A | | 4/1993 | Potter |
| 5,309,907 | A | | 5/1994 | Fang et al. |
| 5,330,741 | A | | 7/1994 | Smith et al. |
| 5,692,511 | A | | 12/1997 | Grable |
| 5,719,399 | A | | 2/1998 | Alfano et al. |
| 5,865,754 | A | | 2/1999 | Sevick-Muraca et al. |
| 5,952,664 | A | * | 9/1999 | Wake et al. ............. 250/459.1 |

FOREIGN PATENT DOCUMENTS

| EP | 0806650 | 11/1997 |
| WO | WO 93/25145 | 12/1993 |
| WO | WO 95/02987 | 2/1995 |
| WO | WO 98/23206 | 6/1998 |

\* cited by examiner

Primary Examiner—Scott J. Sugarman
Assistant Examiner—Richard Hanig
(74) Attorney, Agent, or Firm—Shlesinger, Arkwright & Garvey LLP

(57) ABSTRACT

A method for collecting data for use in image reconstruction of a tissue being scanned containing cancer cells comprises the steps of providing a source of laser beam; providing a biochemical marker that selectively binds to cancer cells within the tissue; directing the laser beam toward the object being scanned; orbiting the laser beam around the object; providing a plurality of sensors adapted to simultaneously detect the laser beam after passing through the object; and limiting the sensors to detect only the radiation released by the biochemical marker after having been activated by the laser beam.

10 Claims, 5 Drawing Sheets

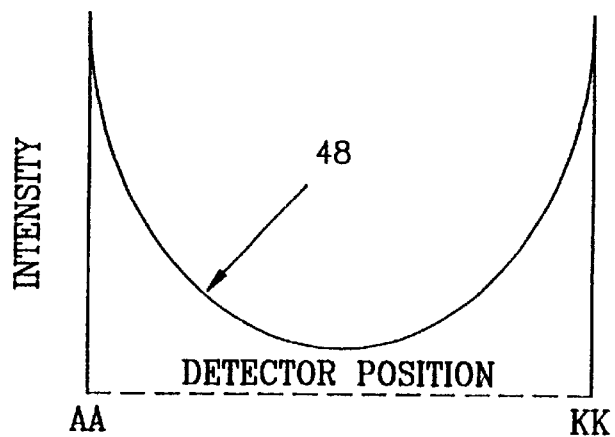
FIG. 5
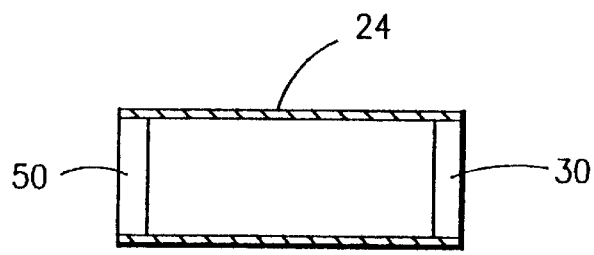
FIG. 6
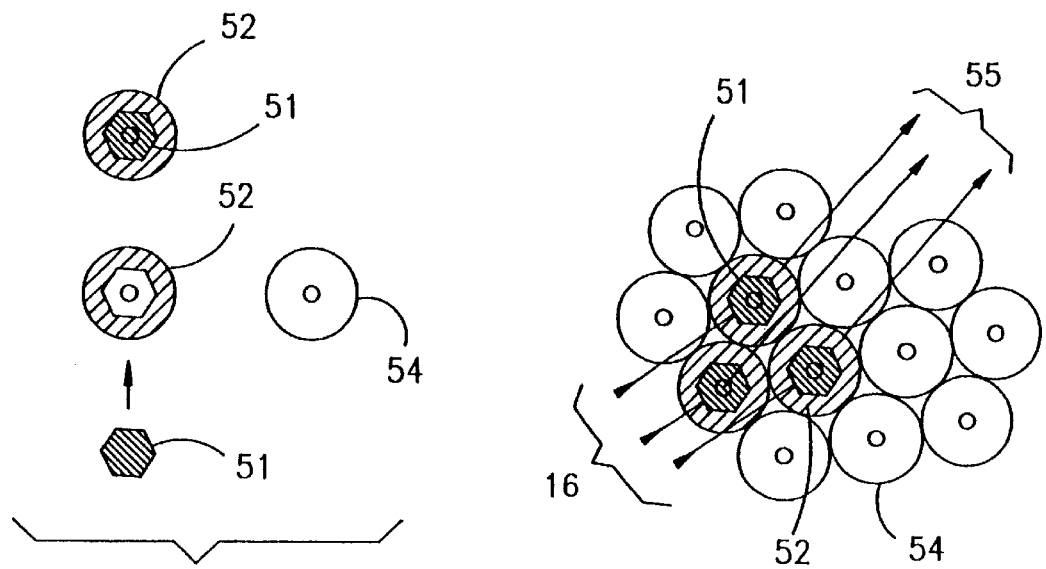
FIG. 7A
FIG. 7B

LASER IMAGING APPARATUS USING BIOMEDICAL MARKERS THAT BIND TO CANCER CELLS

This application is a continuation of International Application No. PCT/US99/04287, filed Apr. 1, 1999, which designates the U.S.

This application is related to provisional applications Ser. Nos. 60/036,088 and 60/063,590, filed on Jan. 17, 1997 and Oct. 30, 1997, respectively, which are hereby incorporated by reference.

This application is also related to U.S. Pat. No. 5,692,511, issued to Richard J. Grable, which is hereby incorporated by reference.

FIELD OF THE INVENTION

The present invention relates generally to a diagnostic medical imaging apparatus that employs a near-infrared laser as a radiation source and more particularly to a method and apparatus for using a biochemical marker that selectively binds to cancer cells and emits radiation when excited different from the apparatus laser beam to provide a positive identification of the cancer site in a reconstructed image of the scanned tissue.

BACKGROUND OF THE INVENTION

Cancer of the breast is a major cause of death among the American female population. Effective treatment of this disease is most readily accomplished following early detection of malignant tumors. Major efforts are presently underway to provide mass screening of the population for symptoms of breast tumors. Such screening efforts will require sophisticates, automated equipment to reliably accomplish the detection process.

The x-ray absorption density resolution of present photographic x-ray methods is insufficient to provide reliable early detection of malignant tumors. Research has indicated that the probability of metastasis increases sharply for breast tumors over 1 cm in size. Tumors of this size rarely produce sufficient contrast in a mammogram to be detectable. To produce detectable contrast in photographic mammogram 2–3 cm dimensions are required. Calcium deposits used for inferential detection of tumors in conventional mammography also appear to be associated with tumors of large size. For these reasons, photographic mammography has been relatively ineffective in the detection of this condition.

Most mammographic apparatus in use today in clinics and hospitals require breast compression techniques which are uncomfortable at best and in many cases painful to the patient. In addition, x-rays constitute ionizing radiation which injects a further risk factor into the use of mammographic techniques as most universally employed.

Ultrasound has also been suggested as in U.S. Pat. No. 4,075,883, which requires that the breast be immersed in a fluid-filled scanning chamber U.S. Pat. No. 3,973,126 also requires that the breast be immersed in a fluid-filled chamber for an x-ray scanning technique.

In recent times, the use of light and more specifically laser light to non-invasively peer inside the body to reveal the interior structure has been investigated. This techniques is called optical imaging. Optical imaging and spectroscopy are key components of optical tomography. Rapid progress over the past decade have brought optical tomography to the brink of clinical usefulness. Optical wavelength photons do not penetrate in vivo tissue in a straight line as do x-ray photons. This phenomena causes the light photons to scatter inside the tissue before the photons emerge out of the scanned sample.

Because x-ray photons propagation is essentially straight-line, relatively straight forward techniques based on the Radon transform have been devised to produce computed tomography images through use of computer algorithms. Multiple measurements are made through 360° around the scanned object. These measurements, known as projections, are used to back-project the data to create an image representative of the interior of the scanned object.

In optical tomography, mathematical formulas and projection techniques have been devised to perform a reconstruction function somewhat similar to x-ray tomography. In order to perform an accurate reconstruction, the location of the points on the scanned object at which data are measured must be known.

In reviewing a reconstructed image of a tissue that has been optically scanned, there is a need to be able to identify the type of objects showing within the tissue. Once the object has been identified and its precise location determined, effective therapy is then initiated based on the photodynamic therapy drugs.

OBJECTS AND SUMMARY OF THE INVENTION

It is an object of the present invention to provide a laser imaging apparatus that uses a biochemical marker to provide a precise location of cancer cells within a tissue being scanned.

It is another object of the present to provide a laser imaging apparatus that uses a fluorophore that binds to cancer cells within a tissue being scanned to provide a precise location of the cancer cells by collecting the radiation intensity emitted by the fluorophore when excited by the laser beam of the apparatus.

It is still another object of the present invention to provide a laser imaging apparatus for imaging a lesion within a tissue and for providing the appropriate wavelength for a laser to activate a photodynamic therapy drug brought to the lesion by a biochemical marker.

It is another object of the present invention to provide a laser imaging apparatus for determining the shortest pathlength between the surface of the tissue and the location of the lesion to allow efficient irradiation by laser energy of a photodynamic therapy drug attached to the lesion.

It is also an object of the present invention to provide a laser imaging apparatus that can detect the presence and location of lesion within a tissue and at the same time providing therapy.

In summary, the present invention provides a method for reconstructing an image of a scanned object, comprising the steps of providing a source of laser beam; providing a biochemical marker that selectively binds to cancer cells within the tissue; directing the laser beam toward the object being scanned; orbiting the laser beam around the object; providing a plurality of sensors adapted to simultaneously detect the laser beam after passing through the object; and limiting the sensors to detect only the radiation released by the biochemical marker after having been activated by the laser beam.

The present invention also provides a method for activating a photodynamic therapy (PDT) drug attached to abnormal cells within a tissue, comprising the steps of providing a biochemical marker carrying a PDT drug within the tissue; scanning the tissue to locate the position of the abnormal cells; determining the shortest path length for a laser beam having a wavelength appropriate for the PDT drug; and directing the laser beam toward the abnormal cells to activate the PDT drug.

The present invention also provides an apparatus for imaging an object, comprising a scanning chamber for receiving therein an object being scanned; a source of laser beam disposed within the scanning chamber for impinging on the object being scanned, the laser beam being adapted to orbit around the object; an array of sensors disposed within the chamber, each of the sensors being adapted to detect radiation emanating from a biochemical marker attached to cancer cells; and a computer programmed to take the output of each detector at every location in the orbit around the object to reconstruct an image of the object.

These and other objects of the present invention will become apparent from the following detailed description.

BRIEF DESCRIPTIONS OF THE DRAWINGS

FIG. 5 is a response curve representing the data points for each of the detectors at each angular position in the orbit of the scanner.

FIG. 6 is an enlarged cross-sectional view of a detector assembly showing an optical filter disposed in front of a photodetector.

FIG. 7A shows a biochemical tag binding with a malignant cell.

FIG. 7B is a schematic view of a colony of cancer cells to which a biochemical marker have bonded and shows the biochemical tag emitting radiation after having been excited by the laser.

DETAILED DESCRIPTION OF THE INVENTION

Figure 1:
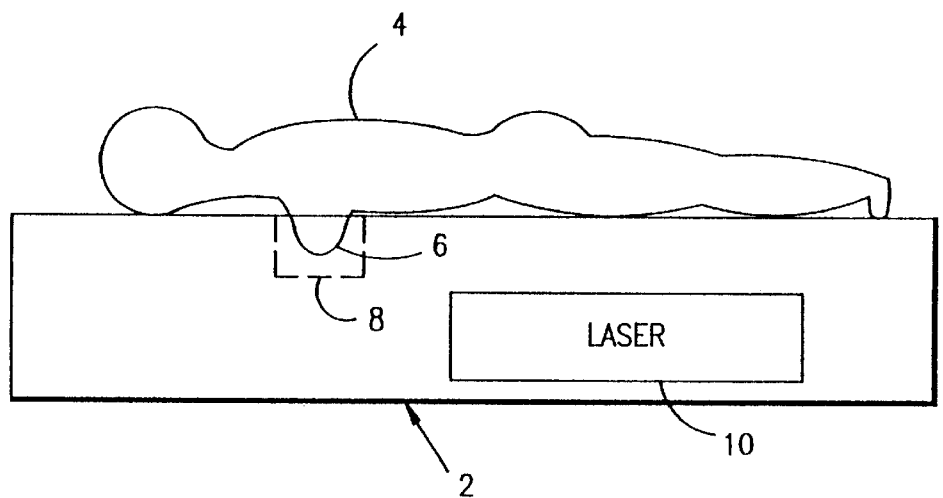
FIG. 1 is a schematic side elevational view of a scanning apparatus including a scanning chamber made in accordance with the present invention, showing a patient positioned on a support platform with her breast pendent within the scanning chamber for optical tomographic study.

A scanning apparatus 2, such as that described in U.S. Pat. No. 5,692,511 is schematically disclosed in FIG. 1. A patient 4 is positioned prone on a top surface of the apparatus 2 with her breast 6 pendent within a scanning chamber 8. A laser beam from a laser source 10 is operably associated with the scanning chamber 8 to illuminate the breast 6.

Figure 2:
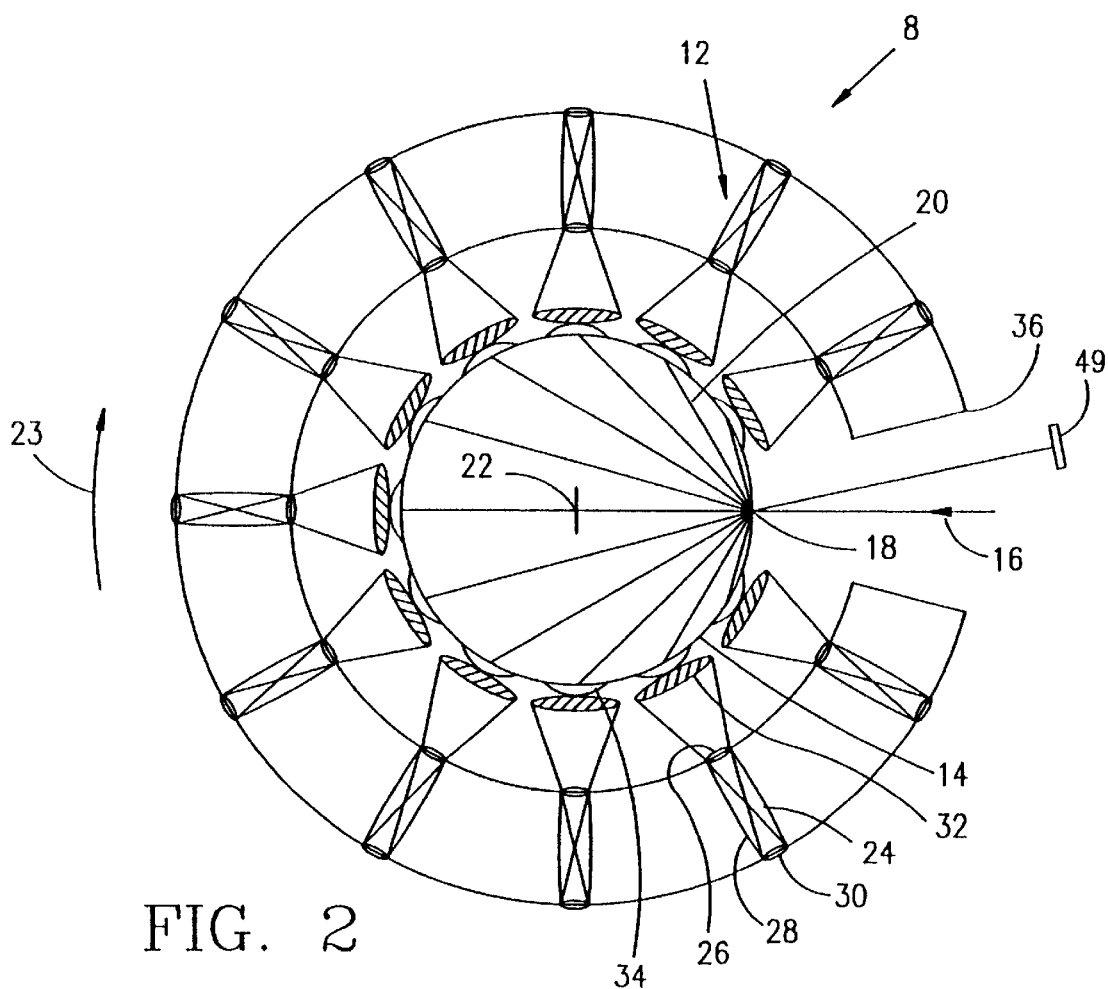
FIG. 2 is a schematic plan view of the scanning chamber of FIG. 1, showing the restricted field of views of the respective detectors and the optical chord lengths of the laser beam through the object.

The scanning chamber 8 is shown schematically in plan view in FIG. 2. The scanning chamber includes a plurality of detector assemblies 12 disposed in an arc to define an opening in which an object 14 to be scanned, such as the breast, is positioned. A laser beam 16 impinges the object at point 18. Light exiting from the object 18, such as the rays 20 is picked up by the respective detector assembly 12, which is then used to provide an image of the scanned object. The rays 20 are represented as chords originating from the point of entry 18 of the laser beam 16 and exiting at various points on the perimeter of the scanned object. The detector assemblies 12 are digitally orbited around the object 14 about an orbit center 22 at equal angular increments for a total angular displacement of 360°. The object is illuminated with the laser beam 16 at each angular position in the orbit 23 and light emerging from the object depicted by the chords 20 on the perimeter of the scanned object, at one instant in time or in a period of time acquired simultaneously, is picked up by the respective detector assemblies 12. Each detector assembly has its longitudinal axis directed toward the orbit center 22. The detector assemblies 12 are secured to a support 36, which is orbited in orbit 23 around the object 14 being scanned. After each complete orbit, the array of detector assemblies 12 and the laser beam 16 are moved vertically to a new position to scan a different slice plane of the object. This is repeated until all the slice planes of the object has been scanned.

Each detector assembly 12 includes an opaque housing 24 with an open front end 26 and a rear end 28 in which a detector 30 is disposed. A fiber-optic cable (not shown) may be used to connect the rear end 28 of the tube to a remotely located detector 30 to advantageously space out the detectors from each other to minimize noise signals. The inside surface of the housing 24 can be tubular, round, square or other cross-sectional shape. The housing 24 is designed to restrict the field of view of its respective detector 30, such that each detector is only looking at its own small area of the scanned object. The field of view of each detector assembly 12 is schematically indicated at 32. A patch or surface seen on the scanned object by the respective detector assembly is schematically indicated at 34.

The field of view 32 and the respective patch of surface 34 are configured such that adjacent patches of surface do not overlap each other. In this way, each detector assembly is uniquely assigned to a patch of surface at each angular position of the orbit so that light coming from one patch of surface could only be detected by the respective detector whose field of view covers that particular patch of surface. Each detector 30 is active to detect any light emerging from its respective patch of surface, since the light beam 16 can course through the object in any paths, such as those depicted by the chords 20. Each housing 24 is further described in a copending application Ser. No. 08/963,760, filed Nov. 4, 1997, which is hereby incorporated by reference.

Figure 3:
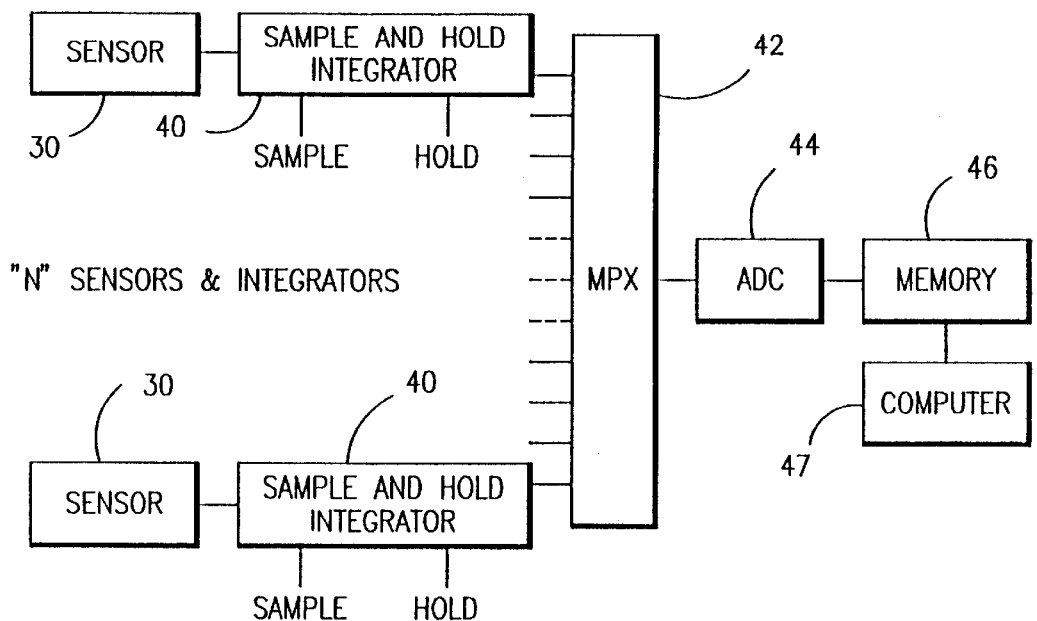
FIG. 3 is a schematic block diagram of a circuit for collecting data from each detector.

Each detector or sensor 30 is operably connected to its respective sample and hold integrator 40, as best shown in FIG. 3. A multiplexer 42 is used to connect the respective integrator outputs to an analog-to-digital converter 44. The digitized individual detector or sensor response is stored in memory 46 for later use in image reconstruction by a computer 47. The circuit allows for simultaneous acquisition of data from all the detectors 30 at each angular position in the orbit of the scanning chamber 8. The sample and hold integrator 40 is further described in a copending application Ser. No. 08/979,328, filed on Nov. 26, 1997, which is hereby incorporated by reference.

Perimeter data of the object being scanned is obtained at each angular position in the orbit of the scanning chamber 8. Several methods are disclosed in copending applications Ser. Nos. 08/965,148 and 08/965,149 filed on Nov. 6, 1997, which are hereby incorporated by reference. One method is to use a sensor array 49 disposed on the same side as the laser beam 16, as best shown in FIG. 2. The laser beam 16 impinges on the scanned object through the center of the orbit. Bright spot is produced at point 18. At each distance from the orbit center, a specific element in the sensor array 49 will detect the bright spot. As the laser beam 16 and the rest of the scanner are orbited around the scanned object about the center, the output signal of the sensor array 49 will be in direct relationship to the perimeter of the scanned object. By acquiring data using one or more known diameters scanned objects, the level of the sensor signal can be calibrated with respect to the scanned object diameters. After calibration, the sensor signal can be electronically decoded to plot the coordinates for the perimeter of the scanned object as the scanner is orbited around the scanned object.

It is advantageous to obtain the perimeter data during data collection of each slice to minimize error due to shifting of the object between slice positions. Perimeter data and the corresponding detector data are used together to reconstruct the image of the object. Perimeter data consist of distances from the center of orbit at each angular position of the orbit.

Figure 4:
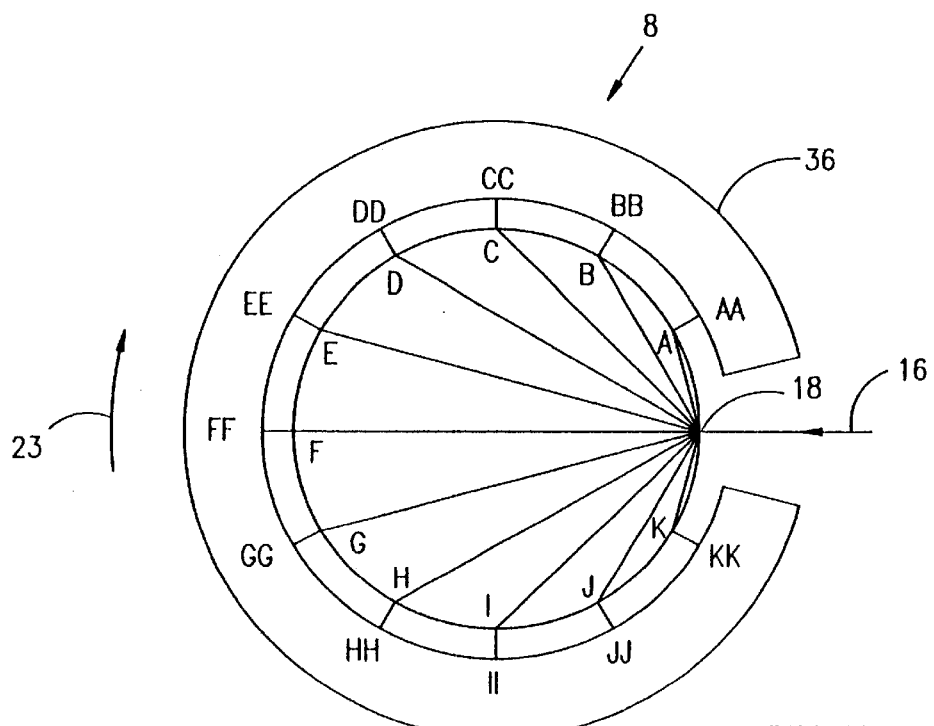
FIG. 4 is a schematic diagram of the scanning chamber of FIG. 2.

The scanning chamber 8 is represented schematically in FIG. 4. The detectors 30 are shown as AA, BB, . . . , KK, indicating their respective positions along the arc. Optical path lengths taken by the laser beam through the object are represented as chords 18-A, 18-B, . . . , 18-K. At each angular position in the orbit 23, the data collected by the detectors AA, BB, . . . , KK are generally indicated by the response curve 48 shown in FIG. 5. The signals seen by the detectors AA and KK are strongest because of the shorter chord lengths 18-A and 18-K. The signal seen by the detector FF is smaller because of its corresponding longer chord length 18-F. It is therefore seen that the signal generally decreases from detectors AA to FF and increases from detectors FF to KK.

The data represented by the curve 48 and the perimeter data at each angular position of orbit are collected simultaneously, until the orbit has traversed a complete circle. Data taken during each orbit of the scanner 8 is used to reconstruct an image of the scanned object using computerized tomographic techniques. Copending application Ser. No. 08/979,624, filed on Nov. 28, 1997, discloses a method for image reconstruction, which is hereby incorporated by reference.

Each detector assembly 12 is provided with an optical filter 50 to limit the spectral response of the detector 30 within the restricted field of view. The filter 50 may be a bandpass filter or cut-off filter. The purpose of the filter 50 will become apparent from the following disclosure.

Figure 8:
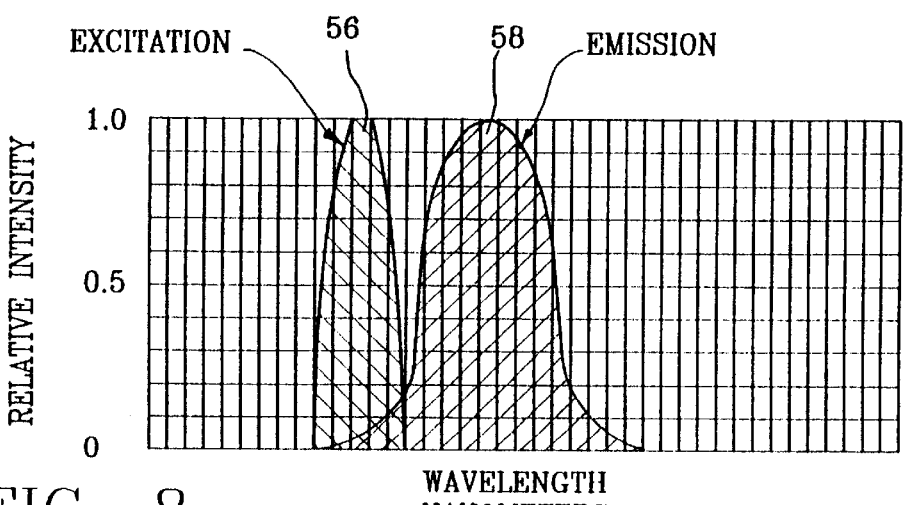
FIG. 8 shows the excitation and emission spectra of a fluorophore as seen by a detector.

A biochemical marker or tag is advantageously used to provide a high signal-to-noise ratio in the response curve 48 and provide precise location of the malignant cells within the breast. The biochemical tag 51 binds with malignant cells 52 within a colony of normal cells 54, as best shown in FIG. 7A. The biochemical tag 50 has a fluorescent characteristic radiation 55 when illuminated by a beam of monochromatic light 16, as best shown in FIG. 7B. The wavelength of the fluorescent radiation is far enough from the excitation beam wavelength, on the order of 5–35 nm, to allow detection of the fluorescent radiation by the detector 30. The excitation beam 16 is represented by the curve 56 and the fluorescent radiation by the curve 58, as best shown in FIG. 8. The optical filter 50 is provided to further enhance the ability of the detector 30 to respond only to those wavelengths that correspond to the emission spectrum 58 of the fluorescent compound.

Figure 9:
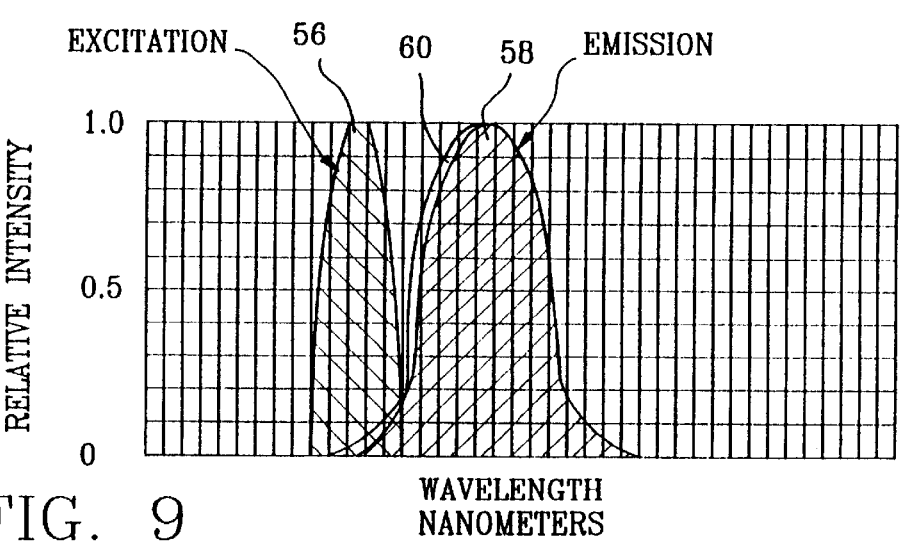
FIG. 9 is similar to FIG. 8, with the emission spectrum modified by a cut-off filter.

Referring to FIG. 9, the filter 50 comprises an optical cut-off filter. The emission spectrum 58 of the fluorescent compound or fluorophore has been modified by the cut-off filter, represented by the area 60, to limit the spectrum range seen by the detector 30. The cut-off filter significantly attenuates wavelengths shorter than the cut-off limit and further isolates the detector 30 from the excitation spectrum 56 while allowing the emission wavelengths to pass through the filter and reach the detector 30.

Figure 10:
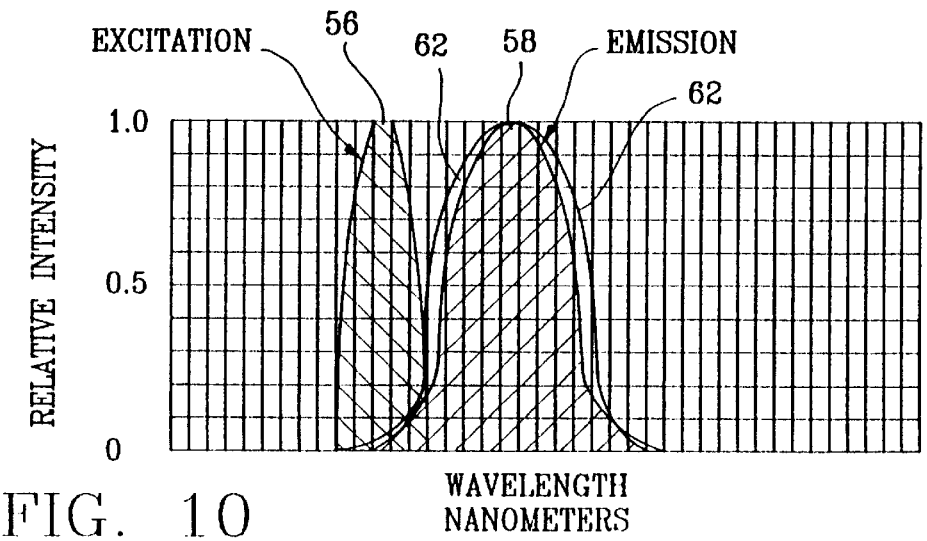
FIG. 10 is similar to FIG. 8, with the emission spectrum modified by a bandpass filter.

Referring to FIG. 10, the filter 50 comprises a band-pass filter to limit the spectral range seen by the detector 30. The band-pass filter modifies the emission spectrum 58 by cutting off wavelengths shorter and longer than the band-pass limits, as illustrated by areas 62 in FIG. 10.

When the fluorescent compound is introduced into the body, it will bind to malignant cells. In breast imaging, introduction of the fluorescent compound into the body will result in specific tagging of malignant cells in the breast. When the breast is irradiated with an intense beam of light at the proper wavelength, the fluorescent compound will emit light at its natural frequency. The detectors 30 in the scanner fitted with optical cut-off or band-pass filters allow only the fluorescent spectrum to stimulate the detector. The optical reconstruction algorithm will display the position of the fluorescence within the boundaries of the scanned breast. Because only the fluorescent compound emits a narrow spectrum of light and the detectors are fitted with appropriate filters to see only this spectrum, a high signal-to-noise ratio is advantageously obtained and precise location of the malignant cells within the breast is possible.

Collagen is a fluorophore with an absorption (excitation) band wavelength of 488 nm and an autofluorescence wavelength of 500+ nm. Peridinin-Chlororophyll, disclosed in U.S. Pat. No. 4,876,190, is another biochemical marker with an absorption (excitation) band wavelength of 440 nm and autofluorescence wavelength of 660 nm.

Figure 11A:
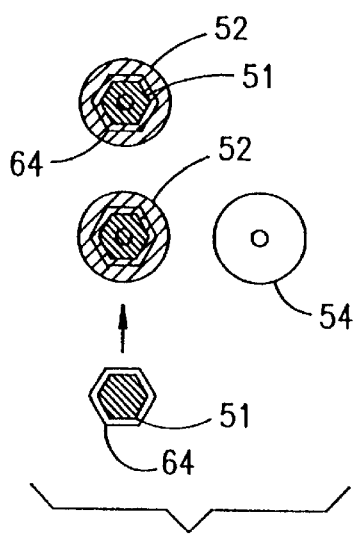
FIG. 11A shows a biochemical tag with an accompanying photodynamic therapy drug binding with a malignant cell.
Figure 11B:
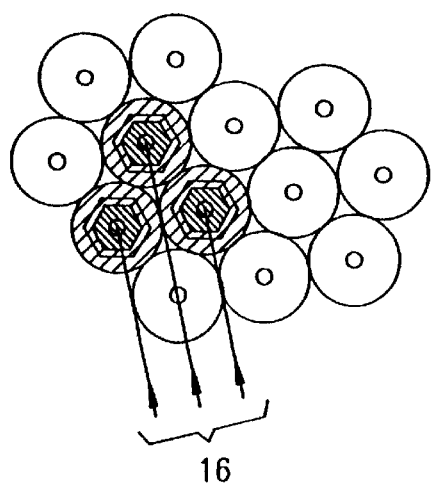
FIG. 11B is a schematic view of a colony of cancer cells to which a biochemical marker carrying a photodynamic therapy drug have bonded and shows activating laser beam impinging on the drug.

Certain drugs, called photodynamic therapy (PDT) drugs can be activated by selected wavelengths of light. It is desirable to limit the area of activation of the PDT drug only to cancer locations. The ability to image the breast to establish location in the breast of suspect areas and the ability to locate fluorescence within the breast provide the basis for therapy planning for PDT. Referring to FIG. 11A, a biochemical tag 51 with an accompanying photodynamic therapy drug 64 is seen to bind with malignant cells 52 within a colony of normal cells 54. The selective nature of the biochemical marker 51 ensures the delivery of the photodynamic therapy drug 62 to the cancer cells 52. The laser source 16 is tuned to provide a specific wavelength for the activation of the PDT drug, as best shown in FIG. 11B. Such a tunable laser is well-known in the art. By knowing the location of the fluorescence, and thus the location of the cancer, determination of the least path for aiming the laser beam 16 to the cancer site is therefore provided for effective therapy.

Lutetium Texaphyrin PCI-0123 (Lu-Tex) is an example of a PDT drug. It has an absorption band wavelength of 732 nm, 90% light absorption in the 723–741 nm wavelength range. It is available from Pharmacyclics, Inc. Photofrin is another example. It has an absorption wavelength of 632 nm, and available from QTL Photo Therapeutics, Inc., Toronto, Canada. Yet another example is long-wavelength water soluble chlorine photosensitizers useful for photodynamic therapy and diagnosis of tumors, disclosed in U.S. Pat. No. 5,330,741, with an absorption wavelength of 600–800 nm.

Figure 12:
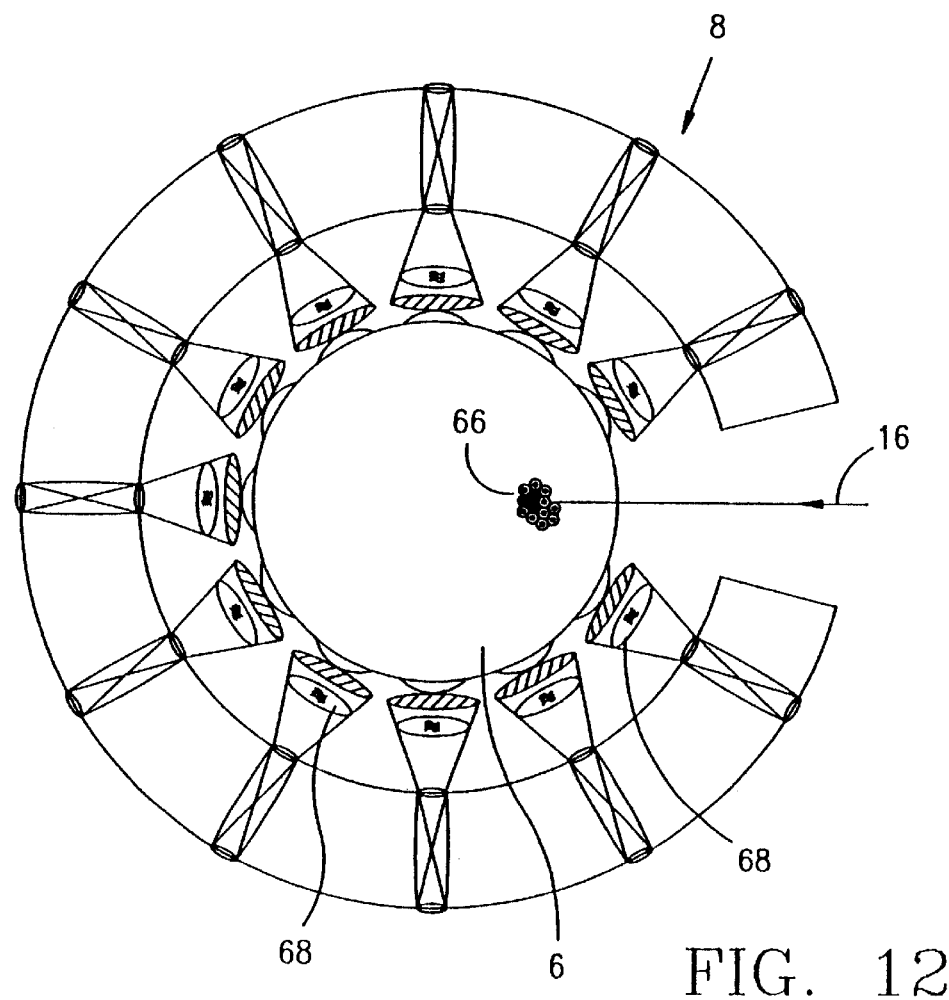
FIG. 12 is a schematic plan view of the scanning chamber of FIG. 1, showing the positioning of the laser beam to provide the minimum path length to a cancer site bearing photodynamic therapy drug transported by a biochemical marker.

Referring to FIG. 12, the breast 6 with a cancer site 66 has been scanned by scanner 8, providing an exact location of the cancer cells due to the fluorescence of the biochemical marker which had attached to the cancer cells. The optical filters 50 are represented schematically at 68. The scanner is then repositioned to provide the shortest path length for the laser beam 16 to the cancer site 64. The wavelength of the laser beam 16 is selected to activate the PDT drug.

While breast cancer detection is the primary focus of the present invention, a person of ordinary skill in the art will understand that it could also be applied to other parts of the body.

While this invention has been described as having a preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. A method for locating cancer cells within a tissue and activating a photodynamic (PDT) drug attached to the cancer cells, comprising the steps of:
   a) providing a tunable laser beam and a plurality of sensors adapted to simultaneously detect radiation exiting from the tissue;
   b) providing a biochemical marker that selectively binds to cancer cells within the tissue, said marker carrying a PDT drug;
   c) scanning the tissue with the tunable laser beam to activate the biochemical marker;
   d) limiting the sensors to detect only the radiation released by the biochemical marker to locate the position of the cancer cells; and
   e) activating the PDT drug with the tunable laser beam directed toward the cancer cells, the tunable laser beam having a wavelength appropriate for the PDT drug.

2. A method as in claim 1, and further comprising:
   a) determining the shortest path length to the cancer cells;
   b) directing the tunable laser beam toward the cancer cells along the shortest path length.

3. A method as in claim 1, wherein said scanning includes orbiting the tunable laser beam around the tissue.

4. A method as in claim 1, wherein said limiting is implemented with an optical bandpass filter operably associated with each sensor.

5. A method as in claim 1, wherein said limiting is implemented with an optical cut-off filter operably associated with each sensor.

6. A method as in claim 1, wherein the biochemical marker is a fluorophore.

7. A method as in claim 1, wherein said scanning includes orbiting the tunable laser beam and the sensors around the tissue.

8. A method as in claim 7, wherein said scanning includes vertically moving the tunable laser beam and the sensors to a new position to scan a different slice plane of the tissue.

9. A method as in claim 1, wherein said scanning includes restricting the field of view of each sensor to a respective small area of the tissue.

10. A method as in claim 8, wherein said scanning includes obtaining perimeter data of the tissue at each slice plane.

* * * * *